United States Patent
Zhao et al.

(10) Patent No.: US 12,370,260 B2
(45) Date of Patent: Jul. 29, 2025

(54) SUPRAMOLECULAR HYDROGEL FOR LIPOPHILIC DRUG DELIVERY, A PREPARATION METHOD THEREFOR, AND USE THEREOF

(71) Applicant: SICHUAN UNIVERSITY, Sichuan (CN)

(72) Inventors: Hang Zhao, Sichuan (CN); Lideng Cao, Sichuan (CN); Yuqi Du, Sichuan (CN); Jian Song, Sichuan (CN); Hang Wang, Sichuan (CN); Qianming Chen, Sichuan (CN)

(73) Assignee: SICHUAN UNIVERSITY, Sichuan (CN)

( * ) Notice: Subject to any disclaimer, the term of this patent is extended or adjusted under 35 U.S.C. 154(b) by 0 days.

(21) Appl. No.: 18/718,353

(22) PCT Filed: Dec. 13, 2022

(86) PCT No.: PCT/CN2022/138626
§ 371 (c)(1),
(2) Date: Jun. 10, 2024

(87) PCT Pub. No.: WO2023/109801
PCT Pub. Date: Jun. 22, 2023

(65) Prior Publication Data
US 2024/0424104 A1     Dec. 26, 2024

(30) Foreign Application Priority Data
Dec. 17, 2021   (CN) .......................... 202111556373.3

(51) Int. Cl.
*A61K 47/24*    (2006.01)
(52) U.S. Cl.
CPC .................. *A61K 47/24* (2013.01)

(58) Field of Classification Search
None
See application file for complete search history.

*Primary Examiner* — Celeste A Roney
(74) *Attorney, Agent, or Firm* — NKL Law; Allen Xue (57) ABSTRACT

A supramolecular hydrogel capable of delivering lipophilic medicaments, a preparation method therefor, and uses thereof are provided. The structure of the supramolecular hydrogel is represented by Formula I, in which $R_1$ and $R_2$ are each independently selected from palmitoyl or oleoyl, respectively. The hydrogel can be used as a drug delivery system, and encapsulate and load various medicaments. In particular, it has good controlled-release for hydrophobic medicaments.

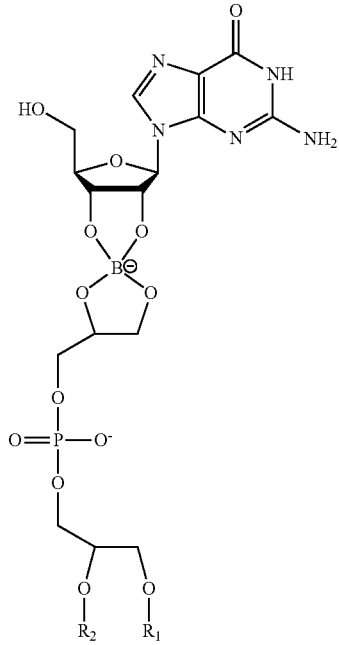

Formula I

13 Claims, 4 Drawing Sheets

SUPRAMOLECULAR HYDROGEL FOR LIPOPHILIC DRUG DELIVERY, A PREPARATION METHOD THEREFOR, AND USE THEREOF

TECHNICAL FIELD

The present invention belongs to the field of biomedical materials, and in particular to a supramolecular hydrogel which can be used for lipophilic drug delivery, a preparation method therefor, and uses thereof.

BACKGROUND

Hydrogel materials can form a hydrophilic polymer network and be expanded by a lot of water or biological fluid, and thereby, the characteristics of hydrogels can allow them to uniquely mimic the physical and biochemical properties of natural biological tissues. Over the years, hydrogels have been widely used in biomedical fields such as cell recruitment, wound healing, tissue engineering and drug delivery.

Among them, supramolecular hydrogels can take advantage of some specific but non-permanent interactions (such as hydrogen bond, x-x stacking, etc.) to synthesize complex hydrogel materials with adjustable and reversible properties. Moreover, because of its excellent stimulation response, self-healing, mechanical properties and so on, supramolecular hydrogels have broad applications, including diagnosis, tissue scaffolds and targeted drug release.

Because gels extracted from natural products usually have good biocompatibility and stimulation response, they have special applications in biomedicine. Nucleic acids (bases, nucleosides and nucleotides) are ideal candidates for supramolecular gels because they are prone to participate in non-covalent reversible interactions. Among them, guanosine and its corresponding nucleoside are widely used as gels, due to the tendency of guanine bases to form stable high-order assemblies, such as G-band, G-tetramer, etc. Using guanosine (guanine nucleoside) and its corresponding nucleosides to prepare supramolecular hydrogels has attracted much attention of researchers. It is found that the supramolecular gels formed by D-guanine nucleoside are easy to crystallize in a short time, resulting in poor stability, which greatly limits its application. Although the stability in vitro of the supermolecular hydrogel formed by L-guanosine self-assembly is improved compared with that formed by D-guanosine self-assembly, it still does not meet the requirements for in vivo application.

How to provide a supramolecular hydrogel with excellent mechanical properties, self-healing, biosafety, drug-loading capacity and in vivo stability is a challenge in the current research.

CONTENT OF THE INVENTION

The object of the present invention is to provide a supramolecular hydrogel capable of delivering lipophilic medicaments, a preparation method therefor, and uses thereof.

The present invention provides a supramolecular hydrogel, and its structure is as represented by formula I:

Formula I wherein, $R_1$ and $R_2$ are each independently selected from palmitoyl and oleoyl.

Further, $R_1$ is palmitoyl, and $R_2$ is oleoyl; alternatively, $R_1$ is oleoyl, and $R_2$ is oleoyl; alternatively, $R_1$ is palmitoyl, and $R_2$ is palmitoyl.

Further, the supramolecular hydrogel is made from guanosine, inorganic base, borate and phosphatidylglycerol as raw materials; the molar ratio of guanosine, inorganic base, borate, and phosphatidylglycerol is (1-10):(1-10):(1-10):(1-10);

preferably, the molar ratio of guanosine, inorganic base, borate, and phosphatidylglycerol is 1:1:1:1.

Further, said inorganic base is selected from the group consisting of LiOH, NaOH, KOH or RbOH; preferably, said inorganic base is NaOH.

Further, said guanosine is D-guanosine or L-guanosine; the structure of D-guanosine is:

the structure of L-guanosine is:

and/or, said borate is $B(OH)_3$, boric acid or 1,4-phenylenediboronic acid;

and/or, the phosphatidylglycerol is palmitoyl-oleoyl-phosphatidylglycerol, dioleoyl-phosphatidylglycerol or dipalmitoyl-phosphatidylglycerol.

Further, the supramolecular hydrogel is obtained by dissolving the raw materials guanosine, inorganic base, borate and phosphatidylglycerol in a solvent under heating and then cooling, in which the concentration of guanosine is 0.02-1 mmol/ml;

preferably, the concentration of guanosine in the supramolecular hydrogel is 0.05 mmol/ml.

Further, the solvent is deionized water.

The present invention also provides a preparation method for the supramolecular hydrogel, which comprises the following steps:

(1) Guanosine, inorganic bases, and borate are dissolved in deionized water and heated until the solution becomes clear;

(2) Phosphatidylglycerol is added to the above solution, and then heated to dissolve and mix well;

(3) Heating is removed, and then the solution is cooled to room temperature to obtain the hydrogel.

The present invention also provides the use of the supramolecular hydrogel mentioned above in the manufacturer of drug carriers;

preferably, the drug is lipophilic.

The present invention also provides a medicament, which is a drug preparation made by using the supramolecular hydrogels mentioned above as drug carriers.

The present invention provides a supramolecular hydrogel, that owns good mechanical properties, injectability, biocompatibility, and drug-loading and release capacities; meanwhile, the hydrogel overcomes the poor stability of the supramolecular hydrogels prepared from guanosine in the prior art, and has excellent in vivo stability. The hydrogel of the present invention can be used as a drug delivery system, and encapsulate and load various drugs. In particular, it has good controlled-release for hydrophobic drugs, and thereby has excellent application prospects.

Obviously, based on the above content of the present invention, according to the common technical knowledge and the conventional means in the field, other various modifications, alternations, or changes can further be made, without department from the above basic technical spirits.

With reference to the following specific examples, the above content of the present invention is further illustrated. But it should not be construed that the scope of the above subject matter of the present invention is limited to the following examples. The techniques realized based on the above content of the present invention are all within the scope of the present invention.

DESCRIPTION OF FIGURES

FIGS. 1A-1E. The rheological measurement results and general morphology of the supramolecular hydrogel according to the present invention.

FIGS. 2A-2B. Biocompatibility test results of the supramolecular hydrogel according to the present invention.

FIGS. 4A-4E. The experimental results for the drug loading and release capacity of the supramolecular hydrogel according to the present invention.

EXAMPLES

The raw materials and equipment used in the specific examples of the present invention are all known products obtained by purchasing those commercially available.

The scheme for synthesis of the supramolecular hydrogel according to the present invention is as follows:

-continued wherein, PG can be selected from various phosphatidylglycerols, which can be divided into POPG, DPPG, DOPG, etc. according to the different types of fatty acid chains on positions 1 and 2 of glycerol, as shown in Table 1.

TABLE 1

Different phosphatidylglycerols.

| PG phosphatidylglycerol | CAS number | $R_1$ | $R_2$ |
|---|---|---|---|
| POPG | 202070-86-8 | Palmitoyl | oleoyl |
| DOPG | 62700-69-0 | oleoyl | oleoyl |
| DPPG | 67232-81-9 | Palmitoyl | Palmitoyl |

Example 1: Preparation of the Supramolecular Hydrogel According to the Present Invention Firstly, 14 mg of guanosine (0.05 mmol) was added into 800 μl of deionized water, to which were added 100 μl of NaOH solution (0.5 M) and 100 μl of B(OH)$_3$ solution (0.5 M), to prepare a GB solution with a guanosine content of 0.05 mmol/ml. The GB solution was heated to 90° C. until the solution became clear and then hold for about 5 min. Subsequently, palmitoyl-olcoyl-phosphatidylglycerol (POPG) was weighed and added (at the mole equivalent to that of guanosine) to the GB solution, mixed well and maintained at 90° C. for about 10 min, to prepare the solution state of GBPOPG. Heating was stopped, and then the solution was cooled to room temperature, so as to form GBPOPG gel (with a concentration of 0.05 M) after about 5 min.

Example 2: Preparation of the Supramolecular Hydrogel According to the Present Invention Firstly, 14 mg of guanosine (0.05 mmol) was added into 800 μl of deionized water, to which were added 100 μl of NaOH solution (0.5 M) and 100 μl of B(OH)$_3$ solution (0.5 M), to prepare a GB solution with a guanosine content of 0.05 mmol/ml. The GB solution was heated to 90° C. until the solution became clear and then hold for about 5 min.

After that, diolcoyl-phosphatidylglycerol (DOPG) was weighed and added (at the mole equivalent to that of guanosine) to the GB solution, followed by mixing well and keeping at 90° C. for about 10 min, to prepare the solution state of GBDOPG. Heating was stopped, and then the solution was cooled to room temperature, so as to form GBDOPG gel (with a concentration of 0.05 M) after about 5 min.

Example 3: Preparation of the Supramolecular Hydrogel According to the Present Invention 14 mg of guanosine (0.05 mmol) was added into 800 μl of deionized water, to which were added 100 μl of NaOH solution (0.5 M) and 100 μl of B(OH)$_3$ solution (0.5 M), to prepare a GB solution with a guanosine content of 0.05 mmol/ml. The GB solution was heated to 90° C. until the solution became clear and then hold for about 5 min.

Then, dipalmitoyl-phosphatidylglycerol (DPPG) was weighed and added (at the mole equivalent to that of guanosine) to the GB solution, followed by mixing well and keeping at 90° C. for about 10 min, to prepare the solution state of GBDPPG. Heating was stopped, and then the solution was cooled to room temperature, so as to form GBDOPG gel (with a concentration of 0.05 M) after about 5 min.

Example 4: Preparation of the Supramolecular Hydrogel According to the Present Invention 28 mg of guanosine (0.1 mmol) was added into 600 μl of deionized water, to which were added 200 μl of NaOH solution (0.5 M) and 200 μl of B(OH)$_3$ solution (0.5 M), to prepare a GB solution with a guanosine content of 0.1 mmol/ml. The GB solution was heated to 90° C. until the solution became clear and then hold for about 5 min.

Then, palmitoyl-olcoyl-phosphatidylglycerol (POPG) was weighed and added (at the mole equivalent to that of guanosine) to the GB solution. The resultant solution was mixed well and maintained at 90° C. for about 10 min, to prepare the solution state of GBPOPG. Heating was removed, and then the solution was cooled to room temperature, so as to form GBPOPG gel (with a concentration of 0.1 M) after about 5 min.

Example 5: Preparation of the Supramolecular Hydrogel According to the Present Invention 28 mg of guanosine (0.1 mmol) was added into 600 μl of deionized water, to which were added 200 μl of NaOH solution (0.5 M) and 200 μl of B(OH)$_3$ solution (0.5 M), to prepare a GB solution with a guanosine content of 0.1 mmol/ml. The GB solution was heated to 90° C. until the solution became clear and then hold for about 5 min.

Then, dioleoyl-phosphatidylglycerol (DOPG) was weighed and added (at the mole equivalent to that of guanosine) to the GB solution, followed by mixing well and keeping at 90° C. for about 10 min, to prepare the solution state of GBDOPG. Heating was stopped, and then the solution was cooled to room temperature, so as to form GBDOPG gel (with a concentration of 0.1 M) after about 5 min.

Example 6: Preparation of the Supramolecular Hydrogel According to the Present Invention 28 mg of guanosine (0.1 mmol) was added into 600 μl of deionized water, to which were added 200 μl of NaOH solution (0.5 M) and 200 μl of B(OH)$_3$ solution (0.5 M), to prepare a GB solution with a guanosine content of 0.1 mmol/ml. The GB solution was heated to 90° C. until the solution became clear and then hold for about 5 min.

Then, dipalmitoyl-phosphatidylglycerol (DPPG) was weighed and added (at the mole equivalent to that of guanosine) to the GB solution, followed by mixing well and keeping at 90° C. for about 10 min, to prepare the solution state of GBDPPG. Heating was stopped, and then the solution was cooled to room temperature, so as to form GBDOPG gel (with a concentration of 0.1 M) after about 5 min.

Comparative Example 1. Preparation of Other Supramolecular Hydrogels 14 mg of guanosine (0.05 mmol) was added into 800 μl of deionized water, to which were added 100 μl of NaOH solution (0.5 M) and 100 μl of B(OH)$_3$ solution (0.5 M), to prepare a GB solution with a guanosine content of 0.05 mmol/ml. The GB solution was heated to 90° C. until the solution became clear. Heating was stopped, and then the solution was cooled to room temperature, so as to form a supramolecular hydrogel.

The beneficial effects of the present invention were demonstrated by reference to the specific Experimental examples in the following.

Experimental Example 1. Mechanical Properties and Injectability of the Supramolecular Hydrogel According to the Present Invention According to the rheological method, various tests (frequency sweep, strain sweep, shear thinning and self-healing tests) were carried out on the supramolecular hydrogel prepared in Example 1, and the results are shown in FIGS. 1A-1E.

Figure 1A:
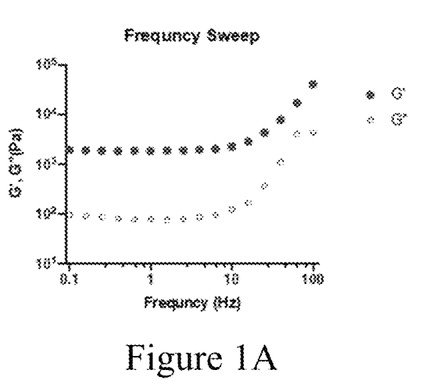
FIG. 1A, the frequency sweep result.
Figure 1B:
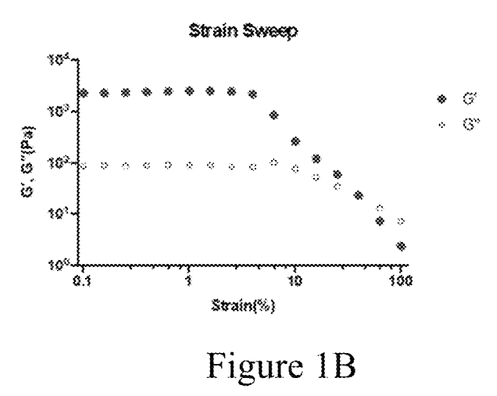
FIG. 1B, the strain sweep result.
Figure 1C:
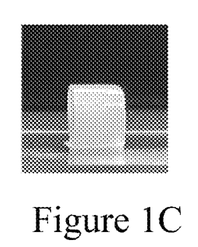
FIG. 1C, solid gel morphology, which is placed in a cylindrical syringe and taken out after gelling.
Figure 1D:
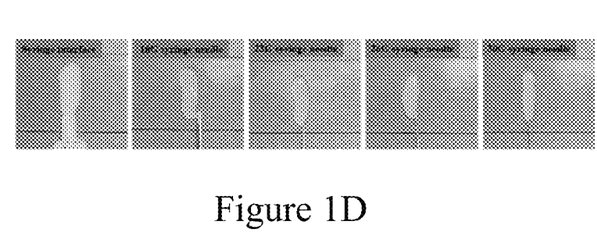
FIG. 1D, the injection states through different aperture syringes.

Measurement method 1: the shear modulus of the hydrogel sample in a flat plate model was measured by a rheometer, and under 0.1% strain condition, frequency was scanned. The frequency range was 0.1-100 Hz. The results in FIG. 1A are obtained, in which 0.1% strain and 1 Hz of frequency correspond to the elastic modulus of 2121.4 Pa.

Figure 1E:
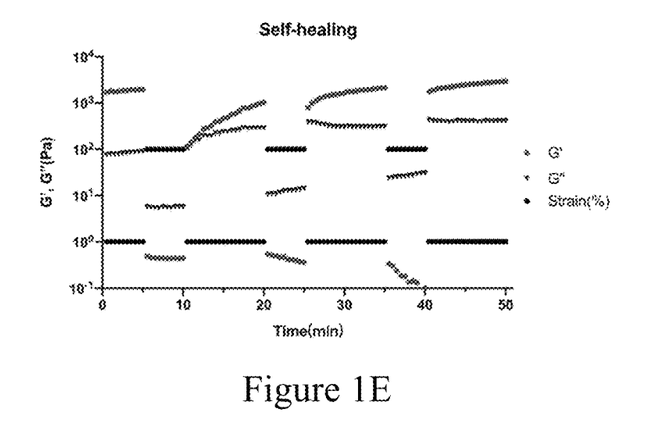
FIG. 1E, the self-healing result of the supramolecular hydrogel.

Measurement method 2: the shear modulus of the hydrogel sample in a flat plate model was measured by a rheometer, and the measurement was divided into seven time periods. The frequency of the whole process was 10 rad/s. The applied strain in the first, third, fifth and seventh time periods was 0.1%, which was used to detect the shear modulus in the gel state; while the applied strain in the second, fourth and sixth time periods was 100%, which was used to simulate the destruction of gel state. It was found that after the gel was destroyed, in the third, fifth and seventh time periods, the gel would slowly recover its original modulus with time, indicating that it had self-healing performance, and the effect diagram in FIG. 1E is obtained.

Based on the Figure, it could be concluded that: 1) the hydrogel had good mechanical properties, with an elastic modulus of 2121.4 Pa (@ 1 Hz, 0.1%); 2) the hydrogel had good self-healing performance; 3) by the syringe injection experiment, the gel had good injectability and could be injected through the smaller aperture of the injection needle.

Experimental Example 2: Biocompatibility of the Supramolecular Hydrogel According to the Present Invention Animal Experiments:
1. Subcutaneous Injection in Mice Female BALB/c mice, 5-6 weeks old, were used to evaluate the in vivo biocompatibility of the supramolecular hydrogel (Example 1) according to the present invention. All experimental animals were raised under conditions of temperature ranging from 22° C. to 26° C., humidity ranging from 40% to 60%, and 12 hours of day and night cycle. After hair-removal treatment on the back of each mouse, 100 μl of Example 1 gel (concentration: 0.05 mmol/ml) was subcutaneously injected, and then the experiment was terminated at a specific time point. The surrounding skin, heart, liver, spleen, lung, kidney and other important organs were collected, fixed in 4% paraformaldehyde, dehydrated, embedded, sectioned, and histologically analyzed by H&E staining.

2. Local Injection of Oral and Maxillofacial Mucosa in Rats

Female SD rats, 4-5 weeks old, are used to evaluate the in vivo biocompatibility of the supramolecular hydrogel (Example 1) according to the present invention. All experimental animals were raised under conditions of temperature ranging from 22° C. to 26° C., humidity ranging from 40% to 60%, and 12 hours of day and night cycle. After anesthesia, each rat was injected with 20 μl of Example 1 gel (at a concentration of 0.05 mmol/ml) under the oral and maxillofacial mucosa. Then, the experiment was terminated at a specific time point. The heart, liver, spleen, lung, kidney and other important organs were collected, fixed in 4% paraformaldehyde, dehydrated, embedded, sectioned, and histologically analyzed by H&E staining.

Figure 2A:
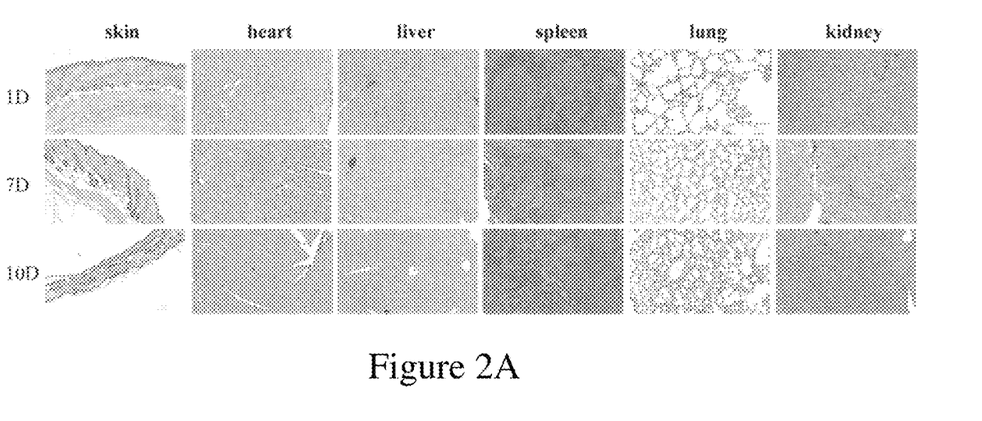
FIG. 2A, toxicity testing of organs in mice after subcutaneous injection (H&E staining)
Figure 2B:
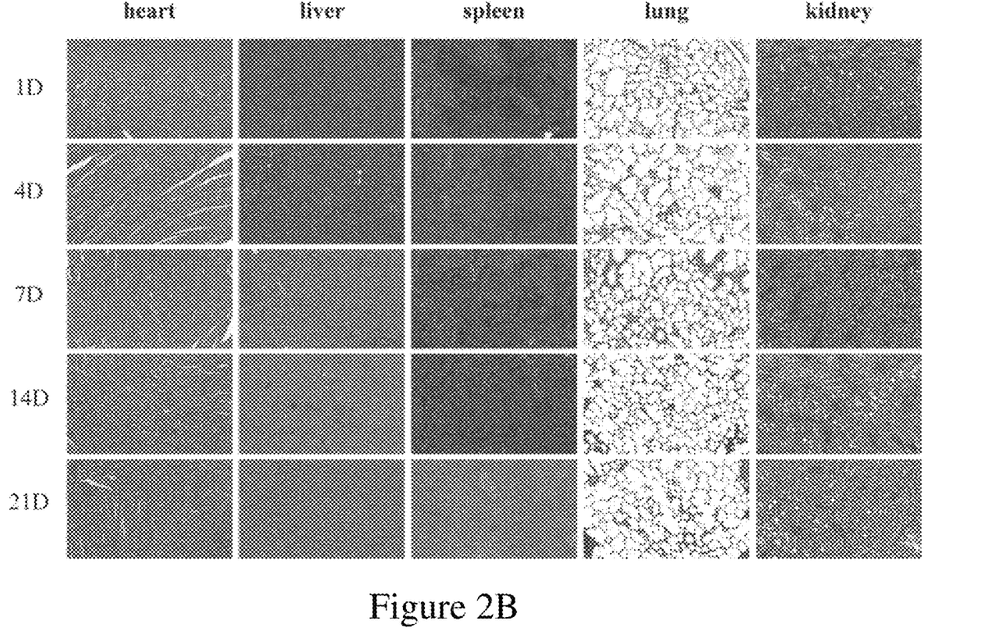
FIG. 2B, toxicity testing of organs after oral submucosal injection in rats (H&E staining).

The biocompatibility results of the supramolecular hydrogel according to the present invention are shown in FIGS. 2A and 2B.

After subcutaneous and oral injection of the supramolecular hydrogel according to the present invention (at a concentration of 0.05 mmol/ml) in animals (mice/rats), it was found that there was no significant organ toxicity, indicating that the hydrogel had good biocompatibility.

Experimental Example 3. In Vivo Stability of the Supramolecular Hydrogel According to the Present Invention Animal Experiments:

Female BALB/c mice, 5-6 weeks old, were used to evaluate the in vivo biocompatibility of the supramolecular hydrogel (Example 1) according to the present invention, the control group supramolecular hydrogel (Comparative example 1), and phosphatidylglycerol solution. All experimental animals were raised under conditions of temperature ranging from 22° C. to 26° C., humidity ranging from 40% to 60%, and 12 hours of day and night cycle. After removing the hair on the back of each mouse, 100 μl of the control group gel, POPG solution and Example 1 gel (their concentrations are all 0.05 mmol/ml) were subcutaneously injected, respectively, and then the experiment was terminated at a specific time point. The amounts of hydrogels under the skin were observed to determine the degradation degrees in vivo.

Figure 3:
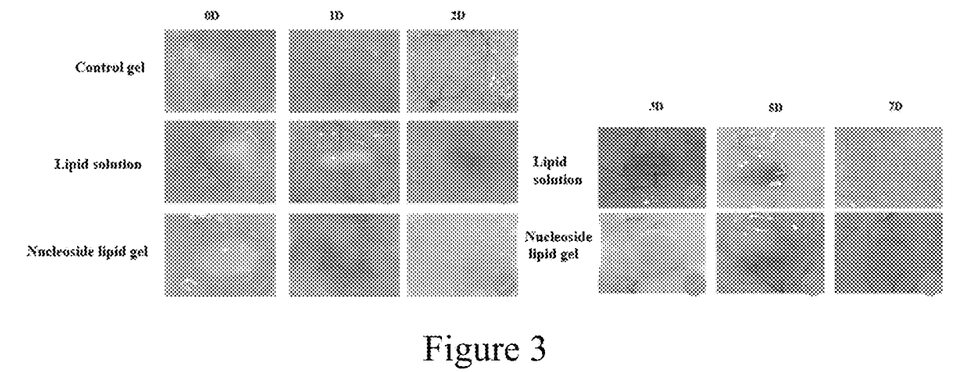
FIG. 3. The test results for in vivo stability of the supramolecular hydrogel according to the present invention.

The in vivo stability results of the supramolecular hydrogel according to the present invention are shown in FIG. 3:

The supramolecular hydrogel (control group gel) without phosphatidylglycerol was completely degraded within 24 hours; the lipid solution in FIG. 3 is the aqueous solution of phosphatidylglycerol (POPG), and its concentration was 0.05 mmol/ml, same as that of the gel. It was found that the phosphatidylglycerol was completely degraded after 3 days in vivo. The results indicated that the stability of the control group gel and the lipid solution was poor, and their degradation was fast. Compared with the control group gel and the lipid solution, it was found that the in vivo stability of the supermolecular hydrogel according to the present invention was greatly increased, and the retention time in vivo could be more than 7 days. It was proved that the supramolecular hydrogel of the present invention had good in vivo stability.

Figure 4A:
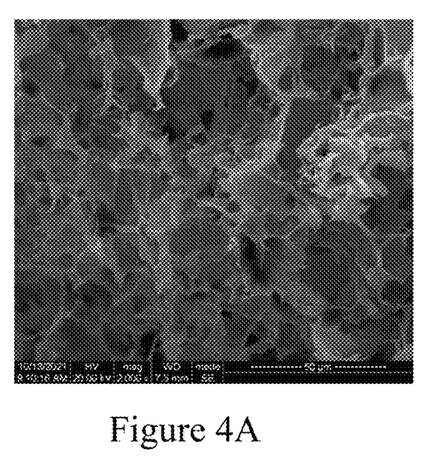
FIG. 4A, the scanning electron microscope (SEM) photograph of the supramolecular hydrogel according to the present invention, showing the porous structure.
Figure 4B:
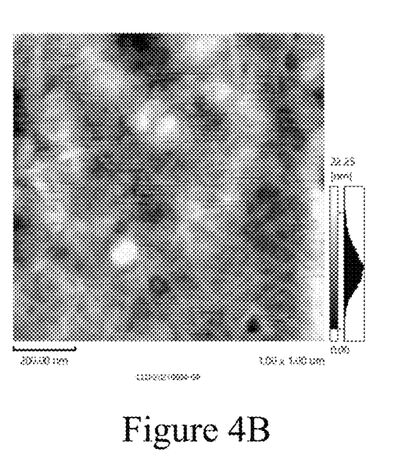
FIG. 4B, the atomic force microscope (AFM) image of the supramolecular hydrogel according to the present invention, showing the filament wound structure.

Experimental Example 4. Loading and Release Capacity of the Supramolecular Hydrogel According to the Present Invention for Liposoluble Drugs Firstly, by scanning electron microscope and atomic force microscope, it was found that the supramolecular hydrogel sample of the present invention had loose porous or filament wound structures (FIG. 4A and FIG. 4B), which confirmed that the gel had the potential of drug loading.

Then, the drug was loaded. The method for drug loading: the prepared hydrogels (Example 1, Comparative example 1) were heated to 90° C. to make it in a solution state, and then the medicament (powder) to be loaded was added into the solution, and mixed with a vortex oscillator or an ultrasonic oscillator. After fully mixing, the solution was naturally cooled to room temperature to form a drug-loaded gel.

1. Firstly, the dye was encapsulated into the hydrogel by the above method for drug loading, and the dye encapsulation was observed. Here, the hydrophilic dye methyl blue and the lipophilic dye Nile red were used for observation, and at the same time, the microstructures of two gels encapsulated with the fluorescent dye Nile red were observed by the laser confocal microscope. The results are shown in FIGS. 4C and 4D.

2. The hydrophilic medicament dexamethasone sodium phosphate, the hydrophobic medicament dexamethasone, and the lipophilic medicament ketoconazole were loaded by the above method for drug loading, and the drug-loaded hydrogel was subjected to the sustained-release test. Specifically, the sustained-release experiment was carried out in a glass vial. 1 ml of gel loaded with 1 mg of medicament was placed at the bottom of the glass vial, above which 3 ml of PBS solution was added as the receiving solution, and then the vial was placed in an oven at 37° C. 500 μl of the receiving solution was taken as a sample at a pre-determined time point, and then the same volume of the receiving solution was supplemented. Subsequently, the drug concentration in the sample collected at each time point was detected by high-performance liquid chromatography (HPLC). The results are shown in FIG. 4E.

Figure 4C:
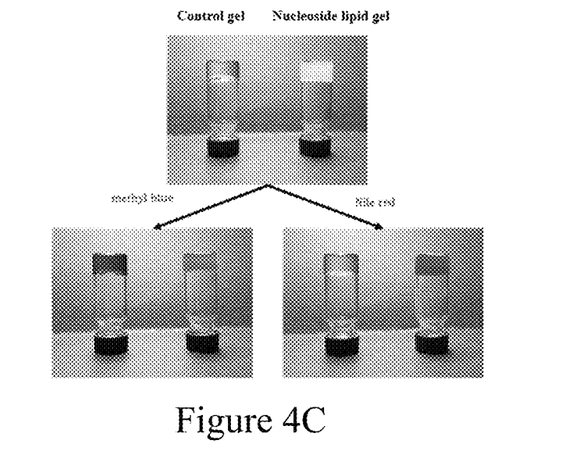
FIG. 4C, the experimental results for encapsulating dyes with the supramolecular hydrogel of the present invention, respectively showing the encapsulation of the hydrophilic dye methyl blue and the hydrophobic dye Nile red.
Figure 4D:
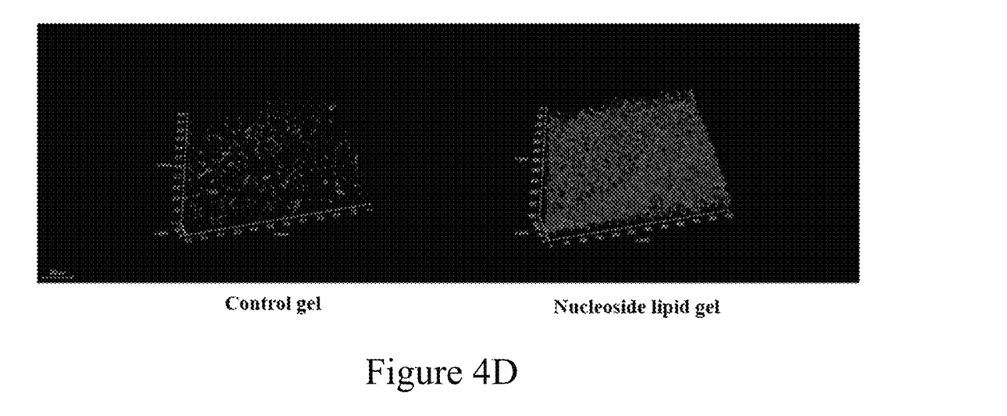
FIG. 4D, the confocal fluorescence microscopy (CFM) image.
Figure 4E:
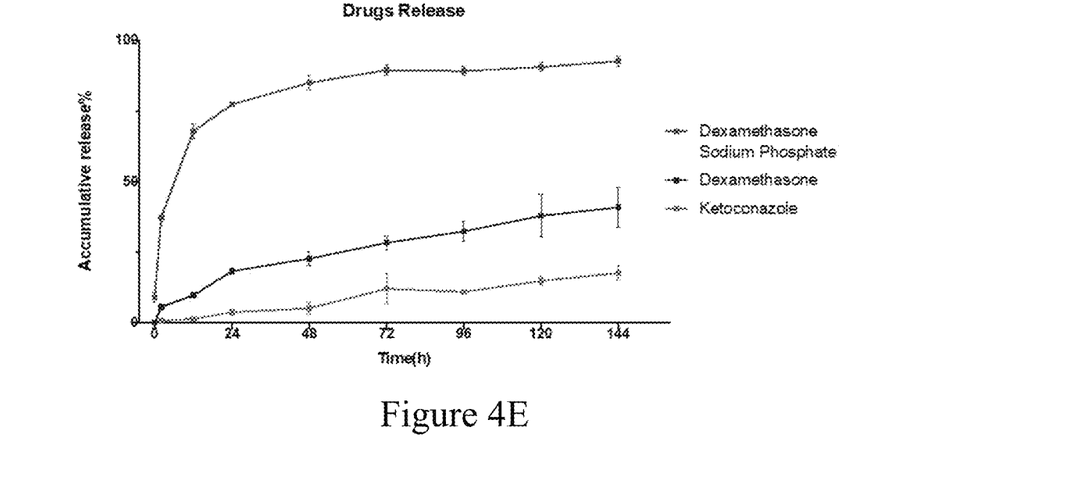
FIG. 4E, the release results of various drugs loaded in the supramolecular hydrogel of the present invention.

According to FIG. 4C, the supramolecular gel of the present invention had good dissolution and dispersion effect for hydrophilic dyes and lipophilic dyes, which was superior to the control gel (Comparative example 1); the laser confocal microscope results showed that compared with the control gel, Example 1 gel had a larger fluorescence area, indicating that it had a wider hydrophobic area (FIG. 4D). Moreover, it was found that the supramolecular hydrogel of the present invention had good release effect for both hydrophilic and lipophilic medicaments, and could continuously release lipophilic medicaments and maintain a certain concentration within 5 days, presenting a sustained release (FIG. 4E).

The study of this Experimental example indicated that the supramolecular hydrogel of the present invention had good loading capacity for hydrophobic and hydrophilic medicaments. The confocal fluorescence microscope and Nile red dye were used to characterize the hydrophobic region in the system, showing there were wide hydrophobic regions in the supramolecular hydrogel system, which could play a good role in the dispersion of lipophilic medicaments.

In summary, the present invention provided a supramolecular hydrogel, that had good mechanical properties, injectability, biocompatibility, and drug-loading and release capacities; meanwhile, the hydrogel overcame the poor stability of the supramolecular hydrogels prepared from guanosine in the prior art, and had excellent in vivo stability. The hydrogel of the present invention could be used as a drug delivery system, and encapsulate and load various drugs. In particular, it had good controlled-release for hydrophobic drugs, and thereby had excellent application prospects.

The invention claimed is:

1. A supramolecular hydrogel of formula I:

Formula I wherein $R_1$ is palmitoyl, and $R_2$ is oleoyl.

2. The supramolecular hydrogel according to claim 1, wherein the supramolecular hydrogel is made from a raw material comprising guanosine, inorganic base, borate, and phosphatidylglycerol, and a molar ratio of guanosine, the inorganic base, the borate, and the phosphatidylglycerol is (1-10):(1-10):(1-10):(1-10).

3. The supramolecular hydrogel according to claim 2, wherein the inorganic base is NaOH or KOH.

4. The supramolecular hydrogel according to claim 2, wherein a concentration of guanosine in the supramolecular hydrogel is 0.02-1 mmol/ml.

5. A preparation method for the supramolecular hydrogel according to claim 1, comprising:
dissolving a raw material comprising guanosine, inorganic base, and borate in deionized water under heating to form a first solution;
dissolving phosphatidylglycerol to the solution to form a second solution; and
cooling the second solution to room temperature to obtain the supramolecular hydrogel.

6. A carrier for a drug, comprising the supramolecular hydrogel according to claim 1.

7. A medicament comprising a drug carrier that is the supramolecular hydrogel according to claim 1.

8. The supramolecular hydrogel according to claim 2, wherein the molar ratio of guanosine, the inorganic base, the borate, and the phosphatidylglycerol is 1:1:1:1.

9. The supramolecular hydrogel according to claim 3, wherein the inorganic base is NaOH.

10. The supramolecular hydrogel according to claim 8, wherein the borate is $B(OH)_3$, boric acid, or 1,4-phenylenediboronic acid.

11. The supramolecular hydrogel according to claim 4, wherein the concentration of guanosine in the supramolecular hydrogel is 0.05 mmol/ml.

12. The medicament according to claim 7, comprising a lipophilic drug compound.

13. The supramolecular hydrogel according to claim 8, wherein the phosphatidylglycerol is palmitoyl-oleoyl-phosphatidylglycerol.

* * * * *